United States Patent [19]

Logothetis et al.

[11] 4,012,709
[45] Mar. 15, 1977

[54] COBALT-MAGNESIUM MONOXIDE ALLOY CERAMIC PARTIAL PRESSURE OF OXYGEN SENSOR

[75] Inventors: Eleftherios M. Logothetis, Birmingham; Kwansuh Park, Ann Arbor, both of Mich.

[73] Assignee: Ford Motor Company, Dearborn, Mich.

[22] Filed: Jan. 12, 1976

[21] Appl. No.: 648,342

[52] U.S. Cl. .................................... 338/34; 73/23; 23/254 E
[51] Int. Cl.² ....................................... G01N 27/12
[58] Field of Search ......... 73/23, 27 R; 324/71 SN; 338/34; 340/237 R; 23/232 E, 254 E

[56] References Cited

UNITED STATES PATENTS

| | | | |
|---|---|---|---|
| 3,732,519 | 5/1973 | Taguchi | 73/27 R |
| 3,951,603 | 4/1976 | Obayashi et al. | 73/27 R |
| 3,952,567 | 4/1976 | Shinagawa | 73/23 |
| 3,953,173 | 4/1976 | Obayashi et al. | 73/27 R |

*Primary Examiner*—Richard C. Queisser
*Assistant Examiner*—Stephen A. Kreitman
*Attorney, Agent, or Firm*—Robert Z. A. Benziger; Keith L. Zerschling

[57] ABSTRACT

A sensor responsive to the partial pressure of oxygen and suitable for inclusion in an internal combustion engine exhaust gas environment is disclosed. The sensor is comprised of a ceramic material fabricated from an alloy of cobalt monoxide and magnesium oxide. The ceramic material exhibits, at elevated temperatures, a direct and generally linear change in the logarithm of its electrical resistance as a function of the partial pressure of oxygen. A body of the cobalt-magnesium monoxide ceramic material is supported by a housing formed of a compatible, nonreactive, ceramic material such as alumina. A pair of electrical leads communicate the sensor ceramic body with an external utilization device. The external utilization device may be arranged to measure the change in resistance of the ceramic sensor body in response to its environment. When the sensor is situated in the exhaust system of an internal combustion engine or a furnace, the change in electrical resistance of the sensor ceramic body is a measure of the partial pressure of oxygen within the exhaust system and is also indicative of the air/fuel ratio of the combustion mixture which has produced the exhaust gases of the sensor's environment. In a preferred embodiment, the external utilization device is arranged to modulate or control the air/fuel ratio of the combustion mixture in response to the sensor.

5 Claims, 11 Drawing Figures

COBALT-MAGNESIUM MONOXIDE ALLOY CERAMIC PARTIAL PRESSURE OF OXYGEN SENSOR

CROSS REFERENCE TO RELATED APPLICATION

This application is an improvement on the invention disclosed in copending, commonly assigned patent application Ser. No. 463,345, filed Apr. 23, 1974 and titled "Air/Fuel Ratio Sensor For Air/Fuel Ratios In Excess of Stoichiometric".

BACKGROUND OF THE INVENTION

1. Field of the Invention

The present invention is directed to the field of internal combustion engine analyzers. More particularly, the present invention is directed to that portion of the above-chemistry of the exhaust gases generated by an engine or a furnace as a measure of the air/fuel ratio of the combustion mixture being provided to the engine or furnace. More particularly still, the present invention is directed to that portion of the above-noted field which is concerned with the measurement of the partial pressure of oxygen within the exhaust gases generated by an internal combustion engine as a measure of the air-to-fuel ratio of the combustion mixture being provided to the engine. With greater particularity still, the present invention is directed to that portion of the above-noted field which is connected with the provision of a sensor mixture by changing an electrical characteristic in response to changes in the partial pressure of oxygen present in such exhaust gases. More particularly still, the present invention is directed to that portion of the above-noted field which is concerned with the provision of a partial pressure of oxygen responsive sensor which may be used within an internal combustion engine exhaust gas environment and which has a range of operation from air/fuel ratios having a fuel content richer than stoichiometry to air/fuel ratios having a fuel cnotent leaner than stoichiometry.

2. Description of the Prior Art

The above-noted copending commonly assigned patent application describes an exhaust gas sensor for use in an internal combustion engine exhaust gas environment. According to the application, the sensor utilizes cobalt monoxide ceramic material, maintained at a temperature in excess of about 900° C, to respond to the partial pressure of oxygen within the exhaust gas produced by a combustion process, maintained, for example in a furnace or an internal combustion engine, operated with an air-to-fuel ratio which is fuel-lean compared to a stoichiometric mixture (hereinafter referred to as a "lean mixture"). The sensor is described as being used as an input device for an air/fuel ratio controller for the associated engine. Such a sensor, while capable of giving satisfactory results, nevertheless is subject to a pair of problems which cause such a sensor to be somewhat impractical as an automotive internal combustion exhaust gas sensor.

The first of these problems is caused by the tendency of cobalt monoxide ceramic material to decompose to form cobalt and oxygen at elevated temperature in the presence of very low quantities of oxygen. This condition is normally found in the internal combustion engine exhaust gases generated by a fuel-rich combustion mixture (hereinafter referred to as a "rich mixture"). For example, decomposition will begin to occur at oxygen partial pressures associated with an air/fuel ratio of about 14 to 1 with decomposition increasing in severity as the air to fuel ratio decreases. Operation of an internal combustion engine in an automotive environment normally entails brief excursions of the cmobustion mixture from a lean mixture to a rich mixture. Such excursions may intentionally occur when the vehicle is started after the engine has cooled to the ambient temperature or upon aaceleration of the vehicle. Such excursions also may occur intentionally under certain other operating conditions and may accidentally occur when the engine is misadjusted or requires readjustment. The decomposition of a cobalt monoxide ceramic material used as an exhaust gas sensor would cnostitute a catastropic failure of the system and must be avoided.

The successful performance of the cobalt monoxide ceramic material sensor requires that the temperature of the cobalt monoxide ceramic material be maintained at a relatively high temperature to avoid a phase change conversion of the cobalt monoxide (CoO) material to $Co_3O_4$ a material which does not exhibit the desired electrical characteristic dependence on partial pressure of oxygen. This material phase change, which is the second of the above-noted problems, occurs at intermediate levels of elevated temperature in the presence of quantities of oxygen which normally would be associated with engine operation with a lean mixture. As the level of the partial pressure of oxygen increases, the temperature at which the phase change will begin to occur increases. Thus, as the quantity of oxygen would be predicted to increase, as would be the case of lean mixtures having decreasing fuel content, the temperature of the sensor would have to be elevated to prevent the undesired phase change. However, as the phase change is reversible, small operational excursions into lower temperature or elevated partial pressures of oxygen can be tolerated.

Thus, while the sensor described in the above-noted application performs well under certain conditions, partial pressure of oxygen range is too narrow to permit the use of the sensor without additional devices to protect the sensor when engine operation results in a sensor environment which exceeds the range. Furthermore, the minimum operating temperature of the cobalt monoxide ceramic material is very high and lower minimum temperature would be advantageous.

It is therefore an object of the present invention to provide an improved sensor material. It is a further object of the present invention to provide an improved cobalt monoxide based material in which the cobalt monoxide will begin to undergo the phase change to another form of cobalt oxide, which will hereinafter be referred to as the spinel form, at a lower temperature for a given partial pressure of oxygen. It is also an object of the present invention to provide an additive or alloy material for the cobalt monoxide ceramic material which additive or alloy material will not significantly alter the electrical response of the cobalt monoxide ceramic material to changes in partial pressure of oxygen. It is a further and specific object of the present invention to provide an additive or alloy material for inclusion in a cobalt monoxide ceramic material which will increase the ability of the ceramic material to resist decomposition, at elevated temperature, in the exhaust gases generated by combustion of rich mixtures. It is a still further object of the present invention to provide such an additive or alloy material which not substantially alter or diminish the ability of the cobalt monoxide ceramic material to respond electrically to changes in the partial pressure of oxygen of its environment. It is a further and particular object of the present invention to provide a class of material which may be alloyed with cobalt material prior to the fabrication of a ceramic sensor material which behaves electrically as cobalt monoxide ceramic material but which is able to withstand decomposition at elevated temperature in gaseous environments having very low concentrations of free oxygen comparable to the exhaust gases produced by combustion of rich mixtures and which will be resistant to conversion to a spinel form at relatively lower elevated temperatures in the presence of substantially greater quantities of free oxygen as may be present in the combustion gases produced by combustion of lean mixtures. It is also an object of the present invention to provide a process for fabricating such exhaust gas sensor ceramic materials.

SUMMARY OF THE PRESENT INVENTION

The present invention provides an exhaust gas chemistry responsive sensor having, as its active element, a ceramic member comprised of an alloy of a 3dn transition metal monoxide and an alkaline earth monoxide. The presently preferred materials are a cobalt monoxide and a magnesium monoxide alloy. A pair of resistance sensing leads are embedded in or otherwise associated with the ceramic material and communicated to an external electronic utilization means. The sensing ceramic member may also be provided with means for generating heat in the vicinity of the sensing ceramic member to provide for rapidly heating this element to a temperature in excess of its minimum operating temperature.

DETAILED DESCRIPTION OF THE PREFERRED EMBODIMENT

Figure 1:
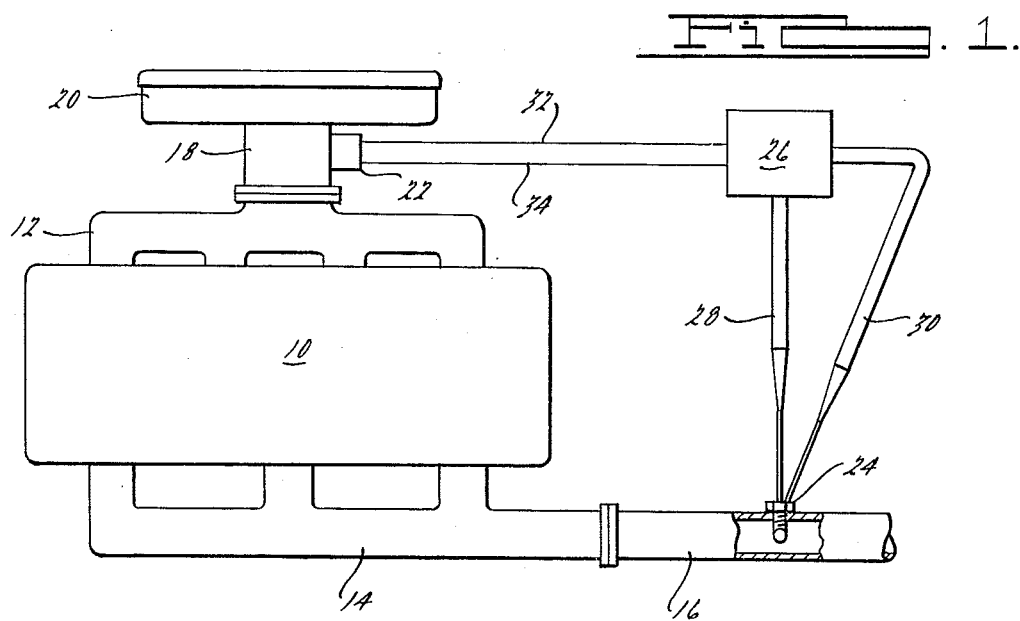
FIG. 1 is a schematic illustration of an internal combustion engine showing the installation of an exhaust gas sensor according to the present invention in the exhaust system thereof.

Referring now to FIG. 1, an internal combustion engine 10 is illustrated. Internal combustion engine 10 is provided with an intake manifold 12 and an exhaust manifold 14. Exhaust manifold 14 communicates with an exhaust conduit 16. A fuel metering and delivery device 18, which may be for example a fuel injection system or a carbuetor, is illustrated schematically communicating with the intake end of intake manifold 12. Fuel metering and delivery device 18 is provided with an air cleaner 20 such that air ingested by engine 10 through intake manifold 12 may be drawn from the atmosphere through air cleaner 20 and through at least a portion of the fuel metering and delivery device 18. The construction, purpose and operation of the hereinabove set forth structure is well known and further description is considered to be unnecessary.

Fuel metering and delivery device 18 is also provided with an air/fuel ratio modulator means 22. Air/fuel ratio modulator means 22 may be for example, in the case of an electronic fuel injection system, a variable resistor arranged to control the quantity of fuel delivered to engine 10 in relation to a given quantity of ingested air. In the case of a carburetor, air/fuel ratio modulator means 22 may be a variably positionable metering valve arranged to control the quantity of fuel metered to engine 10 in respect of a given quantity of ingested air. Alternatively, air/fuel ratio modulator means 22 may be arranged to control a variably positionable air valve so that the quantity of air ingested by engine 10 may be modulated as a function of a given quantity of fuel delivered by fuel metering and delivery device 18.

Exhaust gas conduit 16 is provided with an exhaust gas sensor 24 which is mounted on a suitable land or boss formed on conduit 16. Exhaust gas sensor 24 is arranged to expose the exhaust gas chemistry responsive sensing member thereof according to the present invention to the exhaust gases flowing through conduit 16. As used throughout this description, "exhaust gas sensor" is intended to mean a device or apparatus connected to an engine exhaust system for responding to the chemical constituents of the exhaust gases and which may include a solid ceramic body or wafer having an electrical resistance which varies in response to variations in a chemical constituent of the exhaust gases which chemical constituent varies directly with and as a result of variations in the air/fuel ratio of the combustion mixture which produces the exhaust gases as a by-product of combustion. Exhaust gas sensor 24 communicates with electronic control means 26 through a pair of sensing leads 28. A further pair of leads 30 are also illustrated and will be discussed hereinbelow with reference to FIG. 2.

Electronic control means 26 communicates with the air/fuel ratio modulator means 22 through conductive control leads 32, 34. As described hereinbelow with reference to FIGS. 2 and 3, the electronic control means 26 may be arranged to respond to changes in the exhaust gas chemistry which are sensed by exhaust gas sensor 24 to provide control signals for receipt by the air/fuel ratio modulator means 22. These control signals may be arranged to modulate either the air or the fuel content, and hence the air/fuel ratio, of the combustion mixture being provided to internal combustion engine 10 to thereby maintain a desired exhaust gas chemistry. It will be appreciated that the exhaust gas sensor 24 could also be mounted on a suitable land or boss provided on exhaust manifold 14.

Figure 2:
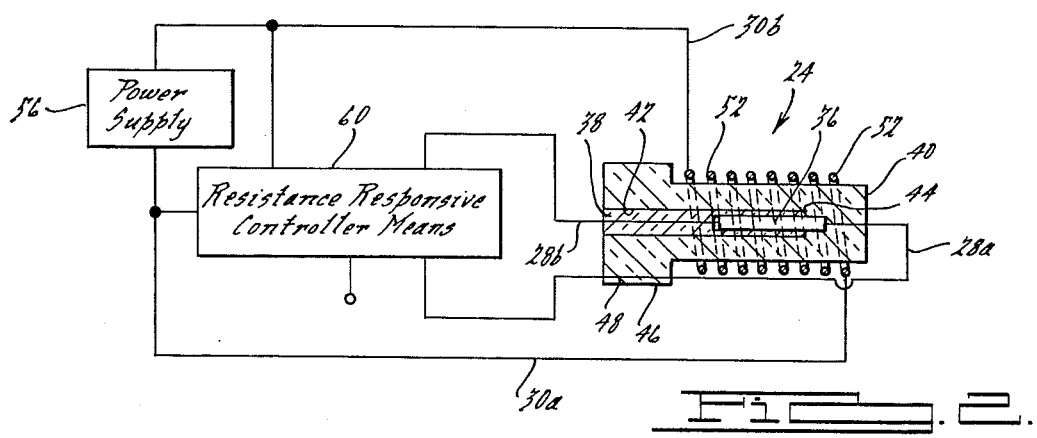
FIG. 2 is a diagrammatic view showing, in a sectional view, one embodiment of the sensor according to the present invention and including a block diagram of an electrical utilization means associated with the sensor for deriving a useful output.
Figure 4:
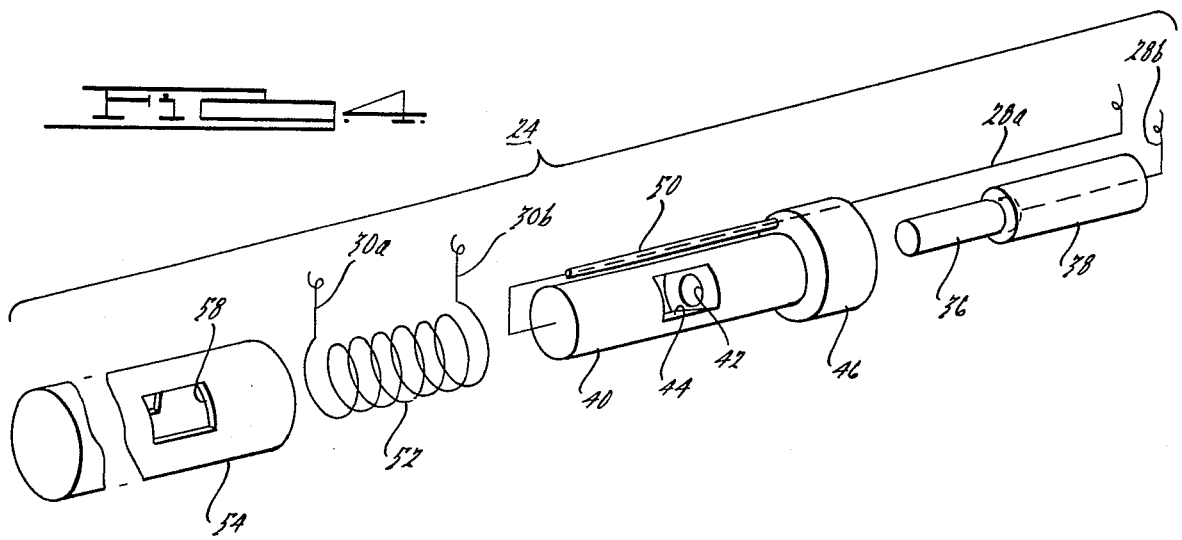
FIG. 4 is an exploded view of one embodiment of the sensor according to the present invention.

Referring now to FIGS. 2 and 4, an exhaust gas sensor 24 is illustrated in a sectional view. An electrical block diagram is also shown to illustrate the various connections between exhaust gas sensor 24 and electronic control means 26. The exhaust gas sensor 24 is comprised of a sensor member 36 formed of a ceramic material according to the present invention. As here illustrated sensor member 36 is in the form of a cylinder or rod of ceramic material supported at its ends by housing members 38, 40. According to the present invention, sensor ceramic member 36 comprises a substantially solid body of cobalt monoxide magnesium ceramic material which is in this instance adapted at its axially remote ends for receipt of the pair of sensing leads 28a, 28b. For example, the axially remote ends of the generally cylindrical sensor member 36 may be provided with an electrode forming coating of platinum paste material and the ends of wires 28a, 28b bonded to these surfaces. Leads 28a, 28b are, preferably also formed of platinum. From the description which follows, and in particular reference to FIG. 6, it will be apparent that other sensor ceramic member geometrys and exhaust gas sensor configurations are contemplated.

In the illustrated embodiment, housing members 38, 40 are generally cylindrical members with housing member 38 sized to be received within a suitable generally axially extending bore 42 provided within housing member 40. Housing member 38 is provided with a support recess arranged to receive one axial end of sensor ceramic member 36. Bore 42 is sized to permit passage of, and to receive, sensor ceramic member 36 upon insertion of sensor ceramic member 36 and housing member 38 within housing member 40. Housing member 40 is also provided with transverse bore or aperture 44 which is arranged to extend completely through housing member 40 and to be positioned to expose sensor ceramic member 36, intermediate the ends thereof, to the gaseous environment of the exhaust gas sensor 24. Transverse bore 44 is therefore operative to provide for communication of a flow of exhaust gases around, and in close proximity to, sensor ceramic member 36. Housing member 40 is also provided with mounting flange 46 having a through passage 48. Hollow support member 50 is received within passage 48. One lead, 28a of the sensing leads 28 is arranged to extend through the hollow support member 50 for electrical communication with one end of sensor ceramic member 36 while the other electrical lead, 28b, of the sensing leads 28 comunicates electrically with the other end of sensor ceramic member 36.

Heating coil 52 is here illustrated as being arranged to surround housing member 40. Each end of heating coil 52 communicates with one lead of the pair of leads 30 (as shown in FIG. 1). This communication may be through flange portion 46, through a separate cover member 54, or through hollow support member 50. The electrical leads 30 are arranged to communicate with an electric power supply 56 for provision of a flow of heating current through heating coil 52.

Cover member 54, as shown in FIG. 4, is arranged to encapsulate heating coil 52 and housing member 40. Cover member 54 therefore provides for protection of the heating coil 52 and of the sensor ceramic member 36 to permit ease of handling of the exhaust gas sensor 24 during its installation in an exhaust system. Cover member 54 also provides for isolation of the heating coil 52 from the cooling effects of the major flow of the exhaust gas stream. Perhaps most importantly, cover member 54 prevents pressure pulses which normally exist within the exhaust gas stream of an internal combustion engine from impingeing directly upon the sensor ceramic member 36. In order to permit communication of exhaust gases within the exhaust stream with the sensor ceramic member 36, cover member 54 is apertured as at 58 with the apertures 58 being positioned to be out of registry with transverse bore 44 when cover member 54 engages mounting flange portion 46.

With particular reference now to FIG. 2, exhaust gas sensor 24 is shown in a sectional view with cover member 54 removed. An electrical system operative with the exhaust gas sensor 24 of the present invention is also illustrated in block diagram. The first pair of electrical leads 28 and the power supply 56 communicate with resistive responsive controller means 60. Upon the application of electric power to heating coil 52, heating coil 52 will operate to elevate the temperature of the sensing element 36 to assist in rapid heating sensing element 32 to its minimum operating temperature. Heating coils 52 could also provide any auxiliary heating for the sensor ceramic member 36 in the event that the selected location for exhaust gas sensor 24 would not normally be at the sufficiently highly elevated temperature to maintain the sensor ceramic member 36 at a temperature in excess of its minimum operating temperature. Under such circumstances, an auxiliary temperature control would also be used.

According to the prior art as represented by the copending commonly assigned application referred to hereinabove, Ser. No. 463,345, now U.S. Pat. No. 3,933,028, a sensor ceramic 36 formed of a cobalt monoxide ceramic must operate at temperatures in excess of about 900° C. This requirement was imposed because, at temperatures below about 900° C and at partial pressures of oxygen characteristic of operation of an internal combustion engine 10 with a lean mixture, cobalt monoxide ceramic material undergoes a phase change to form an oxide of cobalt, the spinel form $Co_3O_4$, which does not exhibit the desired resistance variations. According to the present invention, the minimum operating temperature may be lowered, for example to about 700° C by fabricating the sensor ceramic member 36 from an alloy of a $3d^n$ transition metal monoxide, of which cobalt monoxide is a presently preferred example, and an alkaline earth monoxide, of which magnesium monoxide is a presently preferred example. These materials are alloyed and fabricated to form a cobalt-magnesium monoxide ceramic.

Figure 3:
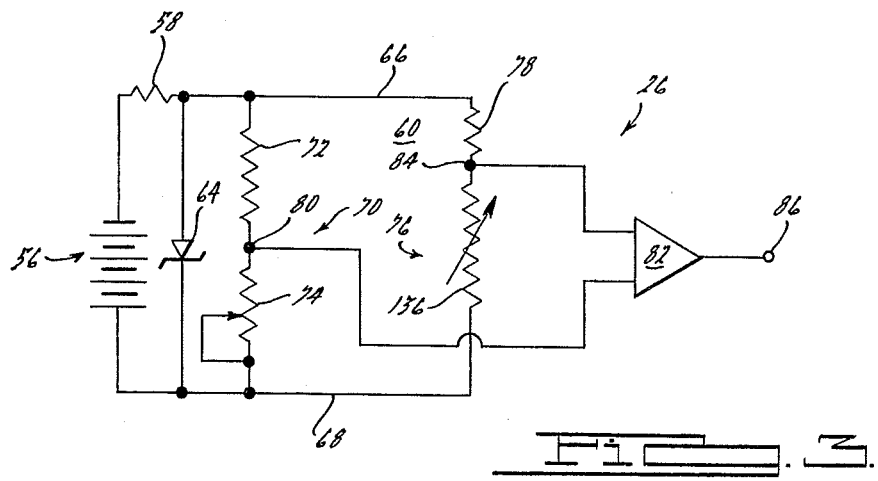
FIG. 3 is an electrical circuit illustrating one element of the block diagram shown in FIG. 2.

Referring now to FIG. 3, a representative circuit for the electronic control means 26 is illustrated. Power supply means 56 is illustrated as a battery and includes a limit resistor 58 and a sener diode member 64 operative to provide a regulated voltage to the resistive responsive controller means 60. In FIG. 3, the variable resistance of the sensor ceramic member 36 is illustrated as a variable resistance 136. Limit resistor 58 and zener diode member 64 are arranged to be cooperative to provide a substantially regulated voltage across the conductors 66, 68. First reference voltage divider 70 is comprised of a fixed resistance 72 and a variable resistance 74, such as for example a potentiometer, connected electrically in series between the conductors 66, 68. Sensor voltage divider 76 is similarly comprised of a fixed resistance 78 connected electrically in series with a variable resistance 136 formed by ceramic sensor member 36. Reference voltage junction 80, formed by the junction of fixed resistance 72 with variable resistance 74, is communicated to one input terminal of operational amplifier 82. Sensor voltage junction 84, formed by the junction of fixed resistance 78 with variable resistance 136, is communicated to the other input terminal of operational amplifier 82. Operational amplifier 82 may be, for example a type $\mu$ 741 operational amplifier. This type of operational amplifier is available through a large number of sources under the above-noted identifying number $\mu$ 741.

Figure 5:
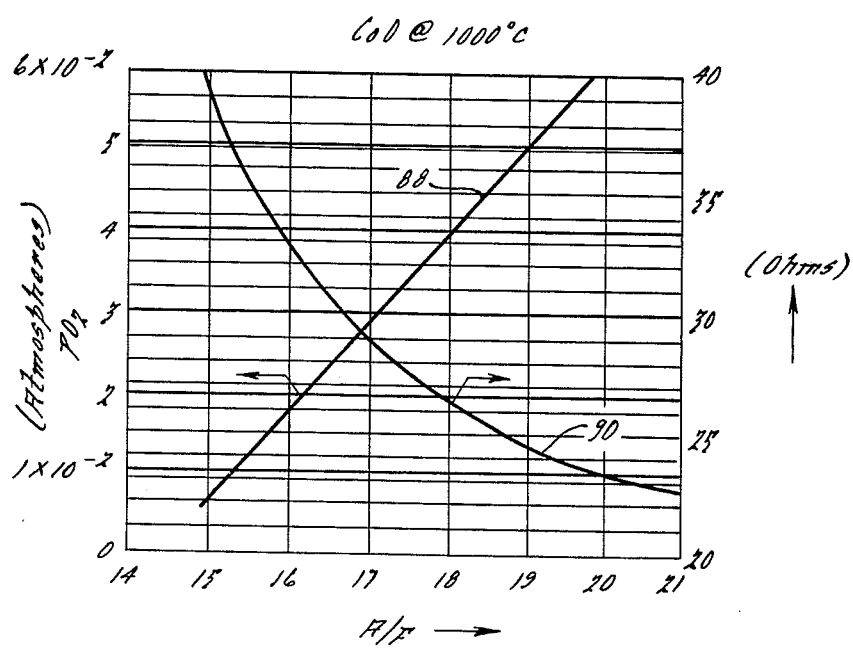
FIG. 5 is a graph illustrating the electrical behavior of the sensor according to the present invention in terms of engine operation.
Figure 5:
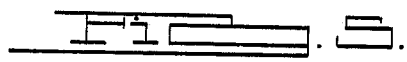

The variable resistance 74 in the reference voltage divider 70 may be calibrated to provide a voltage at reference junction 80 which is exactly equal to the voltage appearing at sensor voltage junction 84 when the partial pressure of oxygen in the atmosphere in which the exhaust gas sensor 24 is immersed is equal to that corresponding to operation of the internal combustion engine 10 with the combustion mixture at the desired air/fuel ratio. By arranging operational amplifier 82 to produce at its output terminal 86 a voltage signal which is a selected multiple of the difference between the voltage values appearing on its input terminal, operational of the internal combustion engine 10 at the precisely desired air/fuel ratio will result in a zero voltage signal appearing at the output terminal 58. Any excursion in the air/fuel ratio of the combustion mixture away from the desired value will result in a shift in the voltage value appearing at sensor junction 84 which, when compared with the voltage appearing at reference voltage junction 80, will result in an output signal appearing at terminal 86. Thus, the signal appearing at output terminal 86, including a zero signal, will indicate the electrical resistance value of sensor ceramic member 36 relative to a preselected value and hence the partial pressure of oxygen in the environment of the exhaust gas sensor 24. The magnitude of the signal appearing at output terminal 86 will be indicative of the magnitude of the variation of the air/fuel ratio from desired value. The polarity of the signal appearing at output terminal 86 will be indicative of the nature of quality of that excursion. For example, a positive polarity signal appearing at output terminal 86 may indicate that the air content of the air/fuel mixture is excessive (resulting in an increase in the air/fuel ratio) while a negative polarity signal appearing at output terminal 86 may indicate that the air content of the air/fuel mixture is inadequate (producing a decrease in the air/fuel ratio of the combustion mixture). The magnitude and the fier 82 may be readily tailored to control air/fuel ratio modulator means 22 such that the polarity and the magnitude of signal appearing at output terminal 86 may automatically command the proper corrective measures to maintain the air/fuel circuitry responsive to output terminal 86 to generate signals for application over leads 32, 34 (FIG. 1) to control air/fuel ratio modulator means 22. Alternatively, if air/fuel ratio modulator means 22 is capable of responding directly to the signals generated at output terminal 86, this terminal may be communicated directly to the air/fuel ratio modulator means, for example, by conductive lead 32. It will be appreciated that the specific electrical network illustrated in FIG. 3 is representative only and that other electrical networks may also be utilized with the present invention to achieve beneficial results. For example, a network comparable to that illustrated in FIG. 3 of U.S. Pat. No. 3,868,846 issued Mar. 4, 1975 and titled "Circuit for Converting a Temperature Dependent Input Signal to a Temperature Independent Output Signal" may be utilized. ting by curve 88, the relationship of the partial pressure of oxygen in volume percent present in the exhaust gases produced by combustion of various air/fuel ratio combustion mixtures. FIG. 5 also includes a graph illustrating by curve 90, typical resistance values for sensor ceramic member 36 accroding to the present invention at the various illustrated air/fuel ratios. It will be appreciated that the values given for the various resistance levels are illustrative only and that specific resistance values will depend upon the particular geometry and dimensions employed for sensor ceramic member 36. However, the illustrated differential resistance is typical. For example, a sensor ceramic member 36 formed of the cobalt-magnesium monoxide alloy ceramic material according to the present invention is larger at an air/fuel ratio of 15 than it is at an air/fuel ratio of 20. Curve 90 is linear if graphed on a logarithmic scale.

Figure 6:
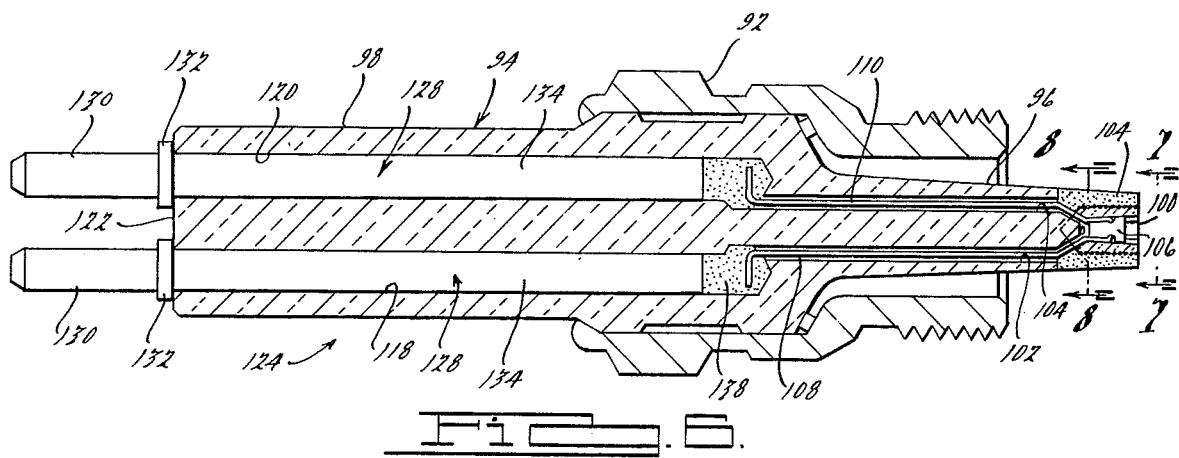
FIG. 6 is a sectional view of an alternate embodiment of a sensor according to the present invention.

Referring now to FIG. 6, a sectional view of an alternative embodiment exhaust gas sensor 124 is illustrated. Exhaust gas sensor 124 is comprised of a metallic outer body 92 and a ceramic insert member or insulator means 94. Ceramic insert member 94 is provided with a first forwardly extending portion 96 and a second rearwardly extending portion 98. First portion 96 is here shown to be conical and is provided with a wafer support slot 100 at the small end of conical or first portion 96. First portion 96 is also provided with a pair of passages 102, 104 which extend rearwardly from slot 100. A wafer 106 of exhaust gas chemistry responsive ceramic material fabricated of cobalt monoxide magnesium alloy ceramic material in accordance with the teachings of the instant invention is illustrated as being received and supported within slot 100. As a matter of convenience in describing positional relationships, forward refers to a direction toward wafer 106 and rearward refers to a direction away from wafer 106. Wafer 106 is provided with a pair of extending electrical leads 108, 110 which extend away from wafer 106 and which are received within passages 102, 104, respectively.

Figure 7:
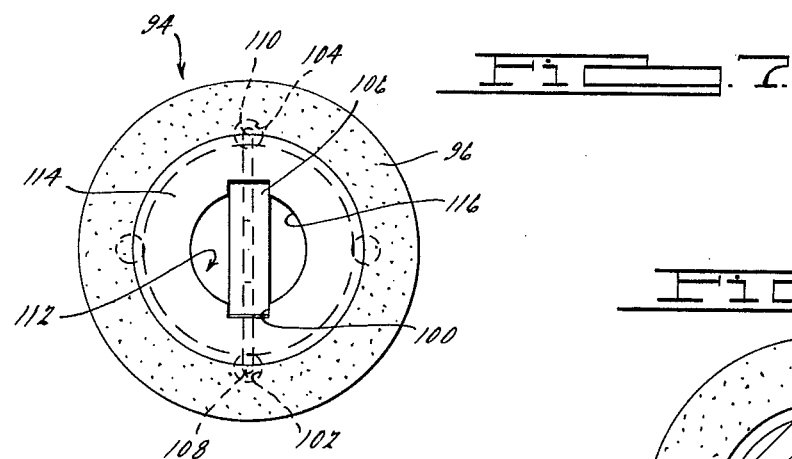
FIG. 7 is an end view of the sensor construction according to FIG. 6.
Figure 9:
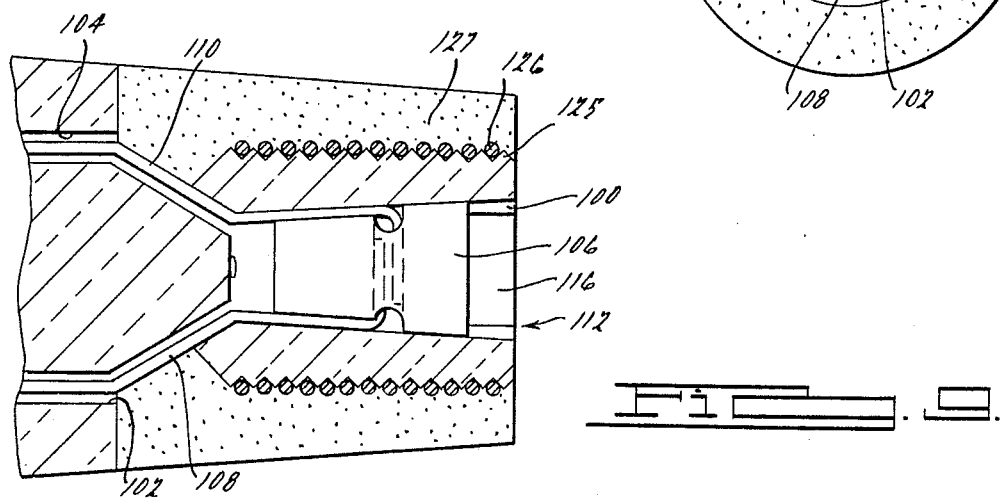
FIG. 9 is an enlarged sectional view of a portion of the sensor according to FIG. 6.

With reference to FIGS. 6, 7 and 9, the forward face 114 of ceramic insert member 94 is shown to be provided with counterbore 112. Counterbore 112 is aligned with and substantially coextensive with slot 100, both of which extend to a depth (rearward from face 114) greater than the comparable dimension of wafer 106. Thus, wafer 106 may be received within slot 100 to a depth which will permit wall 116 of counterbore 112 to operate as shield means to protect the fragile wafer 100 from direct impingement of the pressure pulses of the exhaust gas stream and any particulates which may occur in the exhaust gas stream while allowing counterbore 112 to communicate the gaseous exhaust gas constituents to the wafer 106. The ceramic material of ceramic insert member 94 may readily be formed of a ceramic material sufficiently resistant to the exhaust gas environment to achieve desired operating life criteria, such as, for example alumina ceramic material. The outer surface of wall 116 is shown to be grooved or threaded as at 125. A spiral winding of heater cnoductor 126, such as, for example platinum, is shown received within the groove 125. As with the FIGS. 2 and 4 embodiment, heater 126 may provide for initial heating as well as assuring a minimum operating temperature. An inorganic potting compound 127 such as Saureisen Cement No. 33, or other suitable refractory cement may be used to surround the heater winding 126 in those instances where heating is deemed to be necessary or desirable.

Referring now to FIG. 6, second portion 98 of the ceramic insert member 94 is provided with a second pair of passages 118, 120 which extend from the rearward face 122 of the ceramic insert member 94 and which are positioned to intersect the first pair of passages 102, 104 respectively at a location intermediate the forward face 114 and the rearward face 122. The first pair of passages 102, 104 are sized to receive wafer leads 108, 110 in a loose fit condition. First pair of passages 102, 104 should be sufficiently closely matched to the size of wafer leads 108, 110 to provide lateral support as will be described hereinbelow. The passages 102, 104 may be, for example, of a diameter approximately 10 percent larger than the diameter of wafer leads 108, 110. Second passages 118, 120 are arranged to be substantially larger than passages 102, 104.

A pair of substantially rigid conductive connector pin members 128 are illustrated as being received within second pair of passages 118, 120. Pin members 128 are provided with terminal connector portions 130. These connector terminal portions are arranged to extend rearwardly from rear face 122. Connector pins 128 are provided with abutment shoulders as at 132 which are in contact with rear face 122 following assembly to thereby control insertion depth. Connector pins 128 also include forwardly extending insert portions as at 134 which may be conveniently of generally circular cross section and of a size which closely approximates, but is smaller than, the diameter of the second pair of passages 118, 120 to facilitate insertion therein. Forwardly extending portions 134 are of a length, measured from the abutment shoulder 132, which is slightly less than the depth of the second pair of passages 118, 120 measured from rear face 122.

Figure 8:
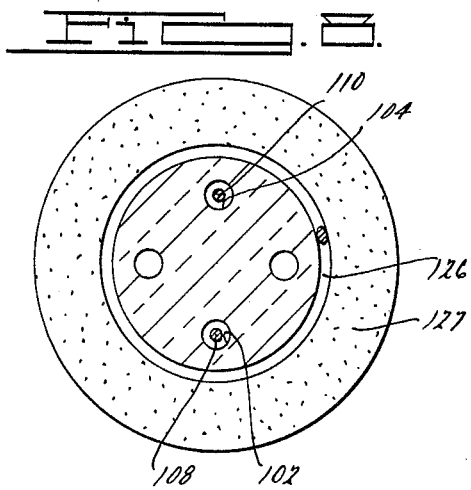
FIG. 8 is a sectional view of a portion of the sensor construction according to FIG. 6.

Referring now to FIGS. 6 and 8, wafer leads 108 110 are shown to be extending through first pair of passages 102, 104 (shown enlarged for convenience) such that a short length of each of the free ends of the wafer leads 108, 110 extends into the forward portion of the second pair of passages 118, 120. The free ends of the wafer leads 108, 110 may be bent over or crimped to extend generally transversely to the axis of the passages. This bending or crimping facilitates retention of wafer 106 within slot 100 during assembly. This also avoids interference between connector pins 128 and water leads 108, 110 during assembly. The void between the forward portions of connector pins 128 and the rearwad portions of wafer leads 108, 110 is filled by conductive glass seal material as at 138. The characteristics of this material as well as the techniques of assembly of an exhaust gas sensor 124 according to this embodiment may be had with reference to copending commonly assigned patent application Ser. No. 609,768 and titled "Stoichiometric Air/Fuel Ratio Exhaust Gas Sensor" and filed in the name of Karen L. Stewart, now U.S. Pat. No. 3,959,765.

According to the present invention, the sensor ceramic member 36 of the FIGS. 2 and 4 embodiment and the sensor wafer 106 of the FIGS. 6, 7, 8 and 9 embodiment are fabricated from a ceramic material having a first component which is a monoxide of a $3d^n$ transition metal and a second component which is a monoxide formed of an alkaline earth. The $3d^n$ transition metals are cobalt, titanium, vanadium, chromium, manganese, iron and nickel while the alkaline earths are magnesium, barium, strontium, calcium. The presently preferred materials are cobalt monoxide and magnesium monoxide. The resulting ceramic material satisfies the general formula $Co_{1-x}Mg_x O$. The value of $x$ may range between 0.01 and 0.99. Preferably $x$ will range between about 0.1 and about 0.95. For automotive internal combustion engine applications, the preferred range for $x$ is from about 0.5 to about 0.8.

The monoxides of titanium and vanadium are metallic at the temperature and partial pressures of oxygen of present interest. Nickel has a much lower concentration of lattice structure defects and therefore has electrical characteristic behavior which is more difficult to reproduce reliably. The monoxides of iron and manganese have much narrower stable ranges than does cobalt monoxide. It will be appreciated that alloys of two or more $3d^n$ transition metal monoxides may be used.

Magnesium monoxide is the presently preferred alkaline earth monoxide for several reasons. The lattice spacing for magnesium monoxide closely approximates the lattice spacing for 3d transition metal monoxides and the ion size for magnesium ($M_g^{++}$) closely approximates the ion size for the $3d^n$ transition metal monoxides. Magnesium forms solid solutions for all values of $x$ in the general formula at useful partial pressures of oxygen and at useful temperatures. It will also be appreciated that alloys of two or more alkaline earth monoxides.

Figure 10:
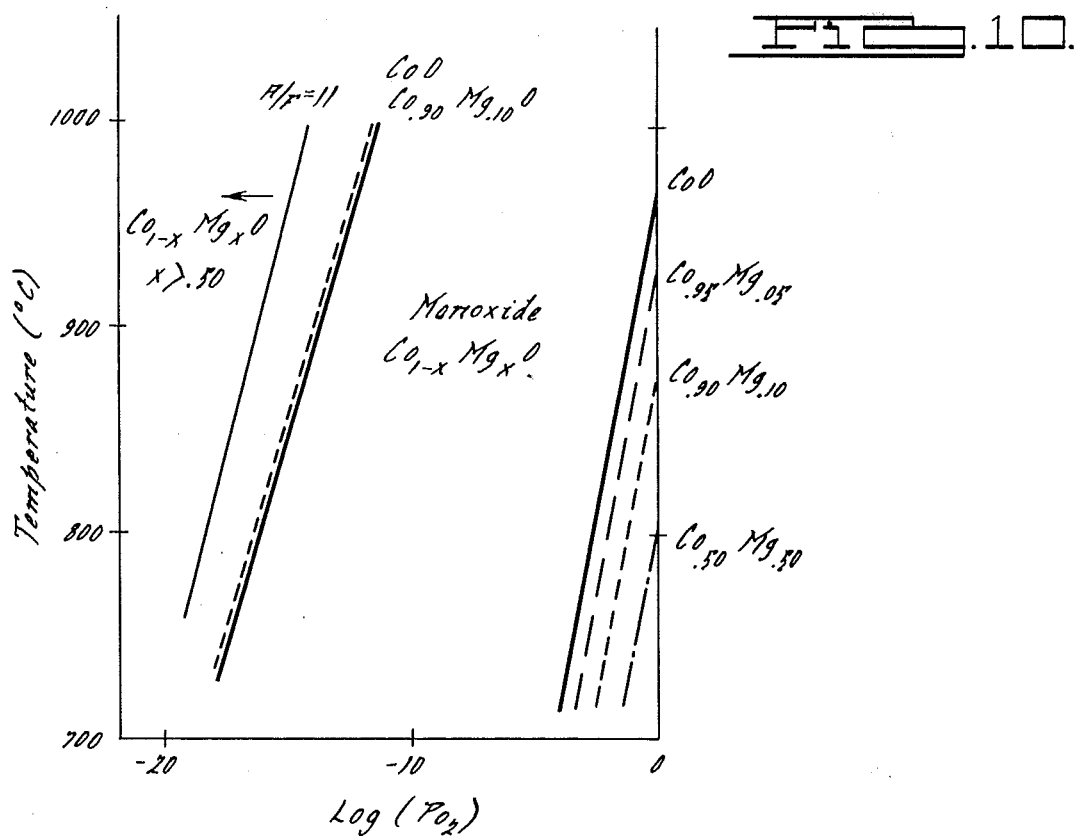
FIG. 10 is a phase diagram illustrating the temperature as a function of the partial pressure of oxygen at which the ceramic material of the sensor according to the present invention undergoes phase change.

Referring now to FIG. 10, a graph illustrating the phase change of the ceramic material is shown. The vertical scale is graphed in terms of temperature expressed in degrees centigrade while the horizontal scale illustrates the log of the partial pressure oxygen. The Figure shows a central region in which the sensor ceramic material according to the formula $Co_{1-x}Mg_xO$ may exist, bounded on the left (or very low partial pressure of oxygen) side by a phase change boundary where the material will give up its oxygen and convert to elemental cobalt and magnesium. The right hand boundary is represented by a family of substantially parallel phase boundaries which represent the temperature/partial pressure of oxygen relationship at which the sensor ceramic will convert to the undesired spinel form. The region between the boundaries is referred to as the "stable region". It can be seen that as the alkaline earth component (as illustrated, magnesium) increases, this phase boundary moves rightward relative to this figure. The left hand boundary for material satisfying the formula $Co_{.90}Mg_{.10}O$ is just slightly leftward from the left hand boundary for CoO material. However, the comparable boundary for material satisfying the formula $Co_{1-x}Mg_x O$ where $x$ is equal to or larger than about 0.5 is off the graph to the left.

The line denoting the relationship between temperature and the partial pressure of oxygen concentration for exhaust gases produced by combustion of a mixture having an air/fuel ratio of 11 to 1 is shown to the left of the stable range for CoO. This ratio represents the practical upper limit of fuel content which may be anticipated or predicted in normal operation of an internal combustion engine. The right hand phase boundary line for material satisfying the formula $Co_{.50}M_{g.50}O$ substantially coincides with the comparable relationship line for a combustion mixture having an air/fuel, ratio of 15 to 1. It can be seen from the graph that, as the magnesium content of the ceramic material increases, the right hand boundary line between the desired sensor ceramic material and the undesired spinel form shifts rearward, relative to FIG. 10. This rightward shift results in a lowering of the temperature at which this phase change occurs for any given partial pressure of oxygen concentration. Thus, with the cobalt and magnesium present in substantially identical quantities, the ceramic material will remain in the sensor ceramic, non-spinel, phase at relatively high partial pressures of oxygen with its temperature maintained at only about 800° C. The non-alloyed cobalt monoxide ceramic material would have to have its temperature maintained above about 950° C to avoid conversion to the spinel form or phase under the same conditions. As the log of the partial pressure of oxygen decreases, the minimum phase change temperature will similarly decrease and, in the region of interest for an internal combustion engine exhaust gas chemistry responsive sensor, the minimum operating temperature may be maintained at 700° C or lower, depending on the anticipated air/fuel ratios (and hence partial pressures of oxygen) for the combustion mixture provided to the internal combustion engine.

Looking to the left hand portion of the FIG. 10 graph (the region corresponding to operation of the internal combustion engine with a rich mixture) it can be seen that the inclusion of an alkaline earth such as magnesium in the ceramic material results on a leftward (relative to the chart) shift of the phase change boundary. Inclusion of a quantity of the alkaline earth in excess of the quantity of the $3d^n$ transition metal will result in a sufficiently large leftward shift to be completely off the FIG. 10 graph. This boundary line corresponds to decomposition of the ceramic material into elemental cobalt, magnesium and oxygen. The leftward shift of this boundary is of significant importance in an exhaust gas chemistry responsive sensor for inclusion in the exhaust gas system of an internal combustion engine since it greatly improves the ability of such a sensor to withstand enrichment transitions of the air/fuel ratio of the combusstion mixture, whether accidental or intentional, as may be occasioned by certain normal operating modes of an internal combustion engine.

Figure 11:
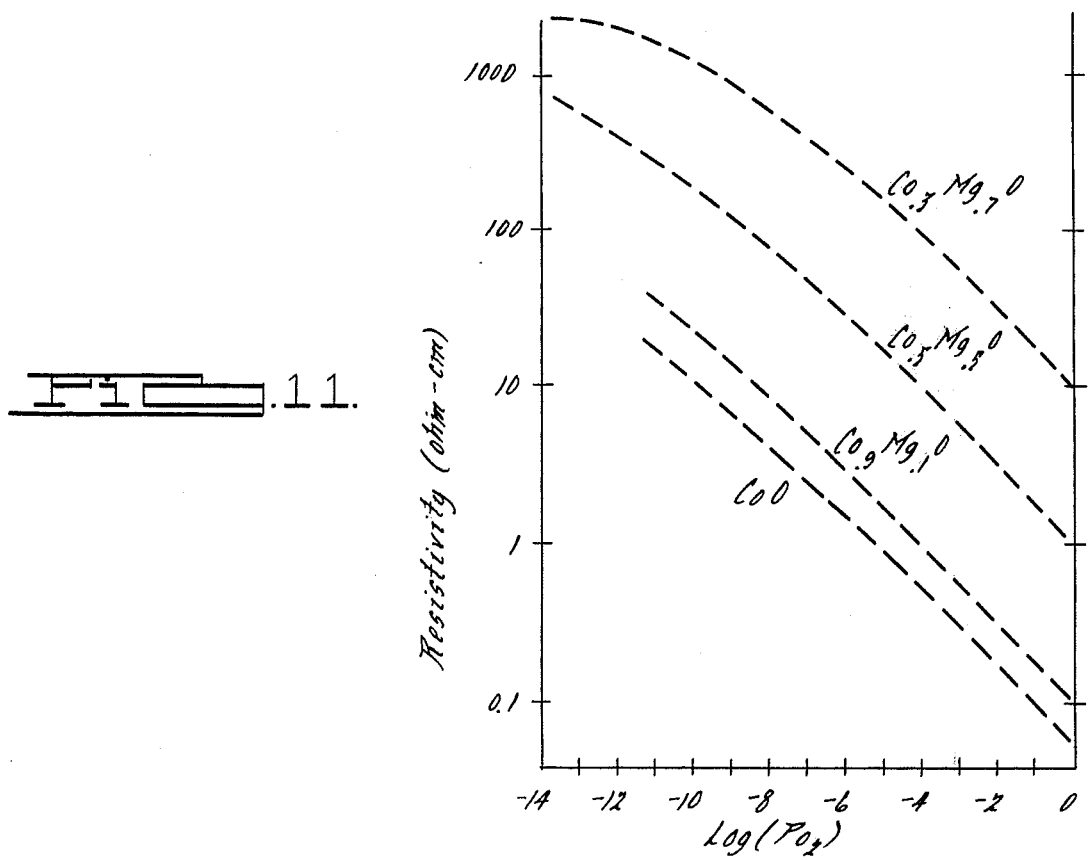
FIG. 11 is a graph illustrating the change in electrical resistance with respect to partial pressure of oxygen for the prior art material as well as for several alloys according to the present invention.

Referring now to FIG. 11, a graph illustrating representative resistance values for sensor ceramic materials fabricated in accordance with the present invention and maintained at a constant temperature of 1000° C is illustrated. The vertical scale is a logarithmic scale of resistivity in ohm-centimeters while the horizontal scale is the negative log of the partial pressure of oxygen. The curve identified as CoO is the curve of the resistivity of cobalt monoxide ceramic material over the range of partial pressures of oxygen as illustrated. The succeeding graphs illustrate the resistance vs. partial pressure of oxygen curves for three different cobalt-magnesium monoxide alloys fabricated to form cobalt-magnesium monoxide ceramic material. These curves illustrate that, as successively greater percentages of magnesium are included, the resistivity of the ceramic material a any given partial pressure of oxygen increases. These curves also illustrate that the resistivity for the fabricated material is a single valued function and is directly related to the partion pressure of oxygen of its immediate environment.

The alloys, and particularly the cobalt-magnesium monoxide alloys, may be prepaed by a wide variety of techniques. However, the simplest and therefore the presently preferred technique is a reaction between the ingredient oxides, that is, cobalt monoxide and magnesium monoxide. These two materials, in powdered form, are milled together by standard ceramic techniques in the proportion of the desired composition and are then prefired in order to obtain a homogeneous end product. The materials are thereafter reground and fired through several cycles. One modification of this process would be to mill the carbonates or oxylates of cobalt and magnesium together instead of milling the oxides together. These materials would thermally decompose during the prefiring treatment in order to result in a cobalt-magnesium monoxide.

After the initial materials have been prepared and prefired the resulting material is then compacted to its final shape. This process may involve the usual ceramic techniques of cold pressing, with or without binder, and subsequent sintering.

An alternate method would be the co-precipitation of the mixed hydroxides of these materials resulting in a readily decomposed compound consisting of an alloy of the desired composition in water. This would result in a product having high purity and homogeneity. This precipitation may be obtained by use of chlorides or nitrides of cobalt and magnesium as starting chemicals.

By alloying a quantity of an alkaline earth monoxide with a $3d^n$ transition metal monoxide to fabricate a ceramic partial pressure of oxygen sensor, the resulting sensor is capable of withstanding very low partial pressure of oxygen excursions of its gaseous environment without decomposing. Furthermore, the resulting ceramic is capable of withstanding relatively high partial pressures of oxygen while being maintained at a lower operating temperature than previous $3d^n$ transition metal oxide ceramic partial pressure of oxygen sensors. An internal combustion engine exhaust gas sensor may thus be fabricated for use with engines designed to operate over a wider range of air/fuel ratios.

We claim:

1. In a partial pressure of oxygen sensor of the type having a ceramic sensor member with an electrical characteristic which varies in response to variations in the partial pressure of oxygen, a ceramic sensing member formed of an alloy of a $3d^n$ transition metal monoxide and an alkaline earth monoxide wherein the ceramic material satisfies the formula $$A_{1-x}B_xO$$

where A is a $3d^n$ transition metal, B is an alkaline earth and $x$ has a value less than about 0.95 and more than about 0.10.

2. A sensor according to claim 1 wherein the value of $x$ in the formula
is less than about 0.80 and more than about 0.50.

3. A sensor according to claim 1 wherein the $3d^n$ transition metal is cobalt.

4. A sensor according to claim 1 wherein the alkaline earth is magnesium.

5. A sensor according to claim 4 wherein the $3d^n$ transition metal is cobalt.

* * * * *